United States Patent [19]

Renfrew

[11] 3,948,938

[45] Apr. 6, 1976

[54] POLYMERIC MATERIALS COLORED WITH YELLOW METHINE DYES AND PIGMENTS

[75] Inventor: Edgar E. Renfrew, Lock Haven, Pa.

[73] Assignee: American Color & Chemical Corporation, Charlotte, N.C.

[22] Filed: May 3, 1974

[21] Appl. No.: 466,847

Related U.S. Application Data

[62] Division of Ser. No. 319,602, Dec. 29, 1972, Pat. No. 3,844,715.

[52] U.S. Cl. ................. 260/315; 8/179; 260/240 R; 260/240 J; 260/240.4
[51] Int. Cl.² ............... C07D 209/82; C07D 403/06
[58] Field of Search ............. 260/315, 240.4, 240 R, 260/240 J

[56] References Cited
UNITED STATES PATENTS

| | | | |
|---|---|---|---|
| 3,655,697 | 4/1972 | Shen et al. | 260/315 |
| 3,687,969 | 8/1972 | Alexander et al. | 260/315 |
| 3,835,152 | 9/1974 | Alexander | 260/315 |

FOREIGN PATENTS OR APPLICATIONS

| | | |
|---|---|---|
| 932,343 | 8/1955 | Germany |
| 1,003,573 | 2/1957 | Germany |

*Primary Examiner*—Arthur P. Demers
*Attorney, Agent, or Firm*—Armstrong, Nikaido & Wegner

[57] ABSTRACT

Polyester fabrics and rigid plastic substrates are respectively dyed and colored with a series of compounds of the formula:

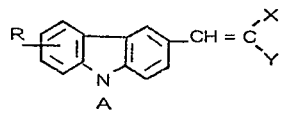

wherein
  R is hydrogen, chlorine, bromine, nitro, or acetamido

A is lower alkyl, benzyl or cyano(lower alkly); each of

X and Y is independently cyano, lower carbalkoxyl, $R_1CO$ OO $R_1$-$SO_2$, $R_1$ being a member selected from the group consisting of lower alkyl, chloro(lower alkyl), bromo(lower alkyl), cyano(lower alkyl), phenyl, (lower alkyl) phenyl, chlorophenyl, bromophenyl, nitrophenyl, cyanophenyl; and X and Y taken together with form a ring containing 5 or 6 ring carbon atoms.

In addition a further series of compounds is provided of the formula

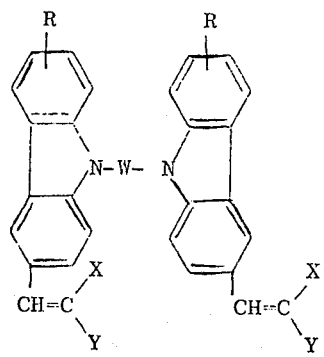

wherein
  W is lower alkylene or p-xylylene;
  R is hydrogen, chlorine, bromine, nitro or acetamido; each of
  X and Y is independently cyano, lower carbalkoxyl, $R_1CO$ or $R_1$-$SO_2$, $R_1$ being a member selected from the group consisting of lower alkyl, chloro(lower alkyl), bromo(lower alkyl), cyano(lower alkyl), phenyl, (lower alkyl) phenyl, chlorophenyl, bromophenyl, nitrophenyl, and cyanophenyl; and
  X and Y taken together form a ring containing 5 or 6 ring atoms.

The above compounds are useful as dyes and, according to a preferred embodiment, colorants for rigid plastic substrates.

5 Claims, No Drawings

POLYMERIC MATERIALS COLORED WITH YELLOW METHINE DYES AND PIGMENTS

This is a division, of application Ser. No. 319,602, filed Dec. 29, 1972, now U.S. Pat. No. 3,844,715.

BACKGROUND OF THE INVENTION

The organic chemist has long known a method for the preparation of certain methine compounds. The preparation of a specific compound in Chemical Abstracts (CA 60 16389f Med. Chemie, Abhandl. Med. Chem. Forschungsstaltten Farbenfabriken Bayer, 7 609–28 (1963)); this compound has only been reported. [Med. Chemie, 7, 609–28(1963)]; this compound has only been reported as a medicinal compound. With the increasing requirments for better dyestuffs for polyester fabrics, as well as the necessity of finding compounds suitable as pigments for rigid plastic substrates, the search for suitable dyestuff compounds has continued in recent years with great activity.

In accordance with the invention, I have discovered methine compounds suitable for the dyeing of polyester fabrics, and particularly for the coloration or rigid plastic substrates.

SUMMARY OF THE INVENTION

In accordance with a first aspect of the invention, a polyester fabric material is provided. The material comprises a polyester fibrous material containing a methine compound of the formula

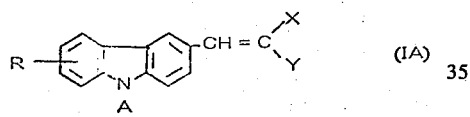

wherein
R is hydrogen, chlorine, bromine, nitro, or acetamido;
A is lower alkyl, benzyl or cyano(lower alkyl); each of
X and Y is independently cyano, lower carbalkoxyl, RCO $R_1$-$SO_2$, $R_1$ being a member selected from the group consisting of lower alkyl, chloro(lower alkyl), bromo(lower alkyl), cyano(lower alkyl), phenyl, (lower alkyl) phenyl, chlorophenyl, bromophenyl, nitrophenyl, cyanophenyl; and
X and Y taken together form a ring containing 5 or 6 ring atoms.

According to a preferred embodiment of the first aspect of the invention, there are provided polyester fabric materials dyed with the above compound wherein R is hydrogen and both X and Y are cyano.

According to a second aspect of the invention, there are provided a novel series of methines of the formula

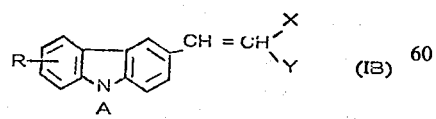

wherein
R is hydrogen, chlorine, bromine, nitro, or acetamido;
A is lower alkyl, benzyl or cyano(lower alkyl);
X is cyano, lower carbalkoxy, RCO or $R_1$-$SO_2$;
Y is lower carbalkoxyl, RCO or $R_1$-$SO_2$; or
X and Y taken together form a ring containing 5 or 6 ring atoms.
$R_1$ is a member selected from the group consisting of lower alkyl, chloro(lower alkyl), bromo (lower alkyl), cyano(lower alkyl), phenyl, (lower alkyl)-phenyl, chlorophenyl, bromophenyl, nitrophenyl, and cyanophenyl.

According to a third aspect of the invention, there are provided a group of rigid plastic substrates which contain a colorant-effective amount of methine compound (I) or a dimeric compound (IB).

According to a fourth aspect of the invention, there are provided dimeric compounds (IV) of the formula

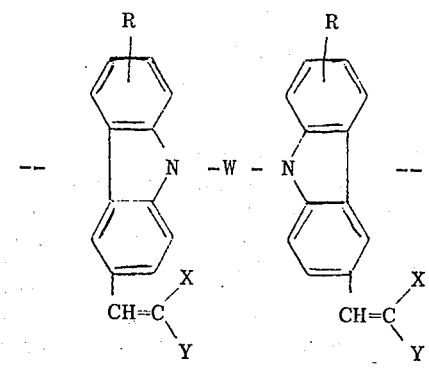

wherein
W is a lower alkylene or p-xylylene;
R is hydrogen, chlorine, bromine, nitro, or acetamido; each of
X and Y is independently cyano, lower carbalkoxyl, RCO or $R_1$-$SO_2$, $R_1$ being a member selected from the group consisting of lower alkyl, chloro(lower alkyl), bromo(lower alkyl), cyano(lower alkyl), phenyl, (lower alkyl) phenyl, chlorophenyl, bromophenyl, nitrophenyl, cyanophenyl; and
X and Y taken together form a ring containing 5 or 6 ring atoms. The compounds described above as the fourth aspect of the invention are also suitable as dyestuffs for synthetic materials including polyesters.

DETAILED DESCRIPTION OF THE INVENTION

The compounds of the first three aspects of the invention may be prepared in the facile manner through the following synthesis. As the starting material may be used an aldehyde of the formula

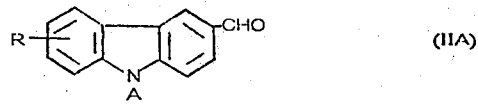

As representative aldehydes (II) may be mentioned the following compound:
9-methylcarbazolyl-3-carboxaldehyde
9-ethylcarbazolyl-3-carboxaldehyde
9-butylcarbazolyl-3-carboxaldehyde
9-benzylcarbazolyl-3-carboxaldehyde
9-hexylcarbazolyl-3-carboxaldehyde
9-ethyl-6-bromocarboxolyl-3-carboxaldehyde
The aldehyde (II) is condensed with a methylene of the formula:

wherein X and Y are as defined above. As representative methylene (III) may be mentioned malononitrile, ethyl cyanoacetate, methylacetoacetate; cyanomethylphenylsulfone, "dimedone", 3-methyl-5-pyrazolone, 1-phenyl-3-methyl-5-pyrazolone and phenylacetonitrile.

In order to prepare a dimeric compound (II) in accordance with the fourth aspect of the invention, the following aldehyde is substituted in the condensation reaction, twice the amount of the methylene (III) used in the condensation reaction:

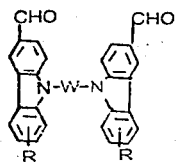

wherein W and R are as defined above.

The starting aldehyde (II) may be produced by adding an appropriate carbazole to dimethylformaide and phosphorus oxychloride at a temperature below about 15°C. Thereafter, the mixture is heated to an elevated temperature, preferably over 90°C, for a period of 1–4 hours. The product is cooled and sodium hydroxy and sodium acetate added thereto. Thereafter an aromatic solvent is added, the resultant solution raised to the boil, and the water removed by azeotropic distillation.

The condensation reaction of the aldehyde (II) and methylene (III) is run at a temperature of 80°–144°C., preferably 100°–125°C, optionally with an alcohol, such as ethanol or 2-propanol, and with a small amount of piperidine. After condensation is complete, which generally requires from about one and one-half to four hours, the reaction mass is slowly cooled to below room temperature, preferably 10°–15°C. The product dye crystallizes slowly from the reaction mixture at these temperatures. The dye is recovered by filtration and is subsequently washed with an alcohol, such as 2-propanol, followed by cold water.

The dyestuffs made by the method of the invention are applied to aromatic polyester fibers in the form of a dispersed color powder or paste, which is obtained by wet milling, in a conventional apparatus such as a ball mill, the dye, a dispersant such as sodium lignin sulfonate, and a wetting agent. The dispersed cake or paste thus obtained can be dried, if desired at 70°–80°C. and thereafter micropulverized. Sufficient dispersant is added to give a dispersed powder containing generally between 25–40 percent by weight active dyestuff base.

The dispersed powder, when added to water with or without auxiliary agents, forms a near collodial aqueous dispersion from which the aromatic polyester fiber or goods is dyed in the conventional manner to give a fiber containing from 0.01–2 percent dyestuff.

The dyes of the invention dye polyester fiber in bright shades and are applied by carrier dyeing, pressure dyeing and thermofixation methods. The dyes also can be used for coloring nylon superpolyamide and cellulose triacetate.

The compounds of the invention may be used for the coloration of rigid plastic substrates. The rigid plastic substrates contemplated within the scope of the invention are those plastic materials capable of being pigmented with the compounds of the invention, and will be referred to herein as "rigid plastic substrates". The rigid plastic substrates of the invention include those materials capable of being formed into a shaped article, including semi-rigid materials which may be deformed by application of pressure.

As rigid plastic substrates of the invention may be mentioned terpolymers, including acrylonitrile-styrene-butadiene, often known as ABS; acrylics, including methacrylics; polystyrene, both foamed and rubber modified; polysulfones; cellulosic derivatives, particularly esters such as cellulose acetate, propionate and butyrate; polyamides such as nylon; epoxy and phenolic resins; polycarbonates; and polyesters. It is understood that the rigid plastic substrates include those materials capable of being pigmented with the compounds of the invention, and therefore copolymers of the above classes of compounds, such as styrene-butadiene, are also within the scope of the invention. Specific examples of thermoplastic resins include polyvinyl chloride, polyvinyl acetate, vinyl chloride/acetate copolymers, polyvinyl alcohol, polyvinyl acetal, ethylene/vinyl acetate, ethylene/vinyl propionate, ethylene/vinyl isobutyrate, ethylene/vinyl alcohol, ethylene/methyl acrylate, ethylene/ethyl acrylate ethylene/ethyl methacrylate, ethylene/allyl alcohol, ethylene/allyl acetate, ethylene/allyl acetone, ethylene/allyl benzene, ethylene/allyl ether, ethylene/acrolein, polyhexamethylene adipamide, polyhexamethylene sebacamide, polycaprolactam, polymethyl methacrylate, polyacrylonitrile, polymethyl acrylate, polyethyl methacrylate, and stryene/methyl methacrylate.

As preferred rigid plastic substrates of the invention may be mentioned the polyacrylates,, polystyrene and polycarbonates.

The rigid plastic substrates are colored with the compounds of the invention through pigmentation processes. The compounds are admixed with the plastic using sets of mixing rollers, mixing or milling apparatus. After the compounds and the plastic have been thoroughly mixed, the resultant colored mixture is shaped into the desired final form through procedures well known to those skilled in the art, such as pouring, calendering, extrusion, spreading, or injection molding. Where the desired product is a semi-rigid material, plasticizers may advantageously be added prior to shaping into the desired final form. As plasticizers suitable for this purpose may be mentioned esters of phthalic acid. Although plasticizer may be incorporated after the mixing of the compound of the invention with the rigid plastic substrate, it also can be incorporated into the rigid plastic material prior to mixing the pigment with the rigid plastic material. In order to vary the strength of the finished product or vary the color, it is also possible to add additional pigments or fillers in an amount sufficient to obtain the desired effect.

The amount of the compound of the invention which is used to color the rigid plastic substrate may vary widely depending upon the degree of color wished to be imparted to the final product, and depending upon whether the compound of the invention is the sole colorant or whether it is used in admixture with other plastic colorants. When the compound of the invention is used in admixture with other colorants, obviously a very minute quantity may be used to produce a complementary effect. Generally, the amount of colorant comprises less than 15%, preferably less than about 8%, by weight in relation to the rigid plastic substrate. An amount of colorant compound which has proved particularly valuable is about 0.0001% to about 1%.

The following examples serve to further illustrate the invention:

EXAMPLE 1

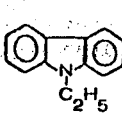

A 500 ml. flask equipped with a stirrer, dropping funnel, thermometer and a cooling bath was charged with 88.0 g dimethylformamide. To this was slowly added at 10°–14°C 50.6 g. phosphorus oxychloride; followed below 15°C by 45.0 g. 9-ethylcarbazole. After the addition was complete, the cooling bath was replaced with a water bath, and the contents of the flask were raised to 91°–94°C and held there for three hours. On cooling the reaction mixture formed a soft crystalline mass. To this in a suitable vessel was added 300 ml ice and water, and slowly, 83 ml. sodiumhydroxide solution, 20% by weight and 265 ml sodium acetate solution, 20% by weight. The pH was 6.3. After three to four hours stirring, the supernatant fluid was drawn off and the waxy residue was washed with three portions, each 1500 water. Then was added 500 ml. toluene.

The toluene solution was transferred to a 1000 ml. 4-neck flask equipped with a stirrer, thermometer, heater, Dean-Starke trap and condenser. The temperature was raised to the boil, and the adherent water was removed by azeotropic distillation, the toluene being returned to the flask. After collection of water had ceased, there was added 16.2 g. malonitrile and 3.0 ml. piperidine. Heating was continued until no more water of reaction was being collected. Then, 160 ml toluene was removed by distillaton, and 100 ml. alcohol was added to the flask. The product separated in yellow crystals, which were collected by filtration, washed with alcohol and dried.

EXAMPLE 2

A ball mill was charged with a portion of the compound of Example 1, an equal Lignosol of a commercially available ligninsulfonic acid dispersing agent ("Lignosol FTA") and enough water to make a mixture 10% in relation to the dye. This mixture was milled to a suitable paste, as shown by filter tests.

The paste when applied in the established ways (carrier, pressure or thermofix) to polyester yielded brilliant greenish yellow dyeings of very good properties especially sublimation fastness and light fastness.

EXAMPLE 3

Methyl methacrylate resin is colored with the compound of Example 1 as the colorant, in a ratio of 2 grams resin to 1 mg colorant. The resin is prepared by placing 1 lb of methyl methacrylate into a Thropp mill (a 2-roller mill), which is then heated and run in order to melt and smash the resin to a molten mass. The compound of Example 1 is added and the entire mixture of resin and colorant is milled until the colorant is uniformly distributed in the mass as measured by eye. While still hot, 30 grams of the hot mass is cut off for use in the following procedure. The sample, containing 30 grams methyl methacrylate and 15 mg. of the compound of Example 1 as colorant, may be conveniently molded in a Laboratory 40 Single Acting Watson-Stillman Laboratory Press (Farrell-Birmingham Co. 50-ton press). 30 grams of methyl methacrylate mixture containing 15 mg. of the compound of Example 1 is placed in the cold mold, which is then closed with the Schrader Valve. The drain is opened and steam is applied to the mold. When steam comes through the drain pipe, the drain is closed. Up to 25.0 tons pressure is exerted on the chips until the mold is fully closed. This can conveniently be accomplished by observing the pressure gauge. When the gauge needle no longer decreases in pressure, then the mold is closed.

The mold is held closed at zero pressure by releasing the hydraulic pressure and maintaining th steam for five minutes. The mold pressure is increased to 10 tons and held for ten minutes, the steam remaining on.

The mold pressure is increased to 15 tons and the steam shut off; the drain is opened and cooling water is added for five minutes. Thereafter the pressure is changed to zero and the mold is opened to extract the resulant plastic chip.

EXAMPLE 4

When the 30 gram mixture of methyl methacrylate and the compound of Example 1 are replaced by 2 pounds polystyrene, 10.44 grams titanium dioxide and 227 mg. of the compound of Example 1, following the procedure of Example 3 a fast coloration of the polystyrene is obtained.

EXAMPLE 5

The compound of Example 1 may also be used as a colorant for plastics made from polycarbonates. A pigmented plastic material of polycarbonates and the compound of Example 1 may be prepared according to the following procedure:

A specimen is prepared by dry mixing pelletized or powdered resin with finely divided colorant until uniform distribution is achieved of the colorant in the resin material. Plasticizer may also be added, if desired. The mixture is then extruded or injected molded under suitable conditions. 454 gms Lexan 121-R (General Electric) pellets are placed in Bipel one ounce reciprocating screw injection molder. The pellets are tumbled for five minutes on the barrel tumbler. The resin is heated (front zone temperature of 550°F and rear zone temperature of 500°F) and chips are produced from the virgin resin until chips of good quality are obtained. When the desired quality of chips are obtained with the clear resin, a fresh batch of Lexan 121-R, containing the compound of Example 1 in an equivalent amount corresponding to Example 2 to produce a pigmented pigmented material is fed into the injection molder, to produce yellow pimented chips having excellent fastness characteristics.

EXAMPLE 6

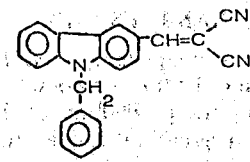

A 1000 ml. 4-neck flask equipped with a stirrer, a thermometer, a heater and a Dean-Starktrap and condenser was charged with 54.2 g. 9-benzyl-3-carbazolecarboxaldehyde. 500 ml. toluene, 14.1 g.

malonitrile and 3.0 ml. piperidine. The mixture was stirred at the boil for five hours; water was collected in the trap and removed from the mixture as formed. The mixture was allowed to cool. The yellow solid was collected on a filter, washed with first toluene, then alcohol, and dried. M.P. 230°–231°C; Analysis: N, found 13.3%; calc. 12.7%.

compounds are obtained. They are suitable for dyeing polyester in accordance with the method of Example 2, yielding dyed polyester fabrics having the color given below. The compounds, when substituted in an equivalent amount for the compound of Example 1 in the process of Examples 3–5, colorations on methyl methacrylte, polystyrene and polycarbonate, respectively, are obtained.

TABLE 1

| Ex. | R | A | X | Y | HUE |
|---|---|---|---|---|---|
| 11 | H | $-C_2H_5$ | CN | CN | Greenish Yellow |
| 12 | H | $n-C_4H_9$ | CN | CN | " |
| 13 | H | $n-C_6H_{11}$ | CN | CN | " |
| 14 | H | $-CH_2-\phi$ | CN | CN | " |
| 15 | H | $-C_2H_5$ | CN | $COOC_2H_5$ | " |
| 16 | H | $-CH_2-\phi$ | CN | $COOC_2H_5$ | " |
| 17 | H | $n-C_4H_9$ | $COOC_2H_5$ | $COOC_2H_5$ | " |
| 18 | H | $n-C_4H_9$ | $CH_3CO-$ | $COOCH_3$ | " |
| 19 | H | $-C_2H_5$ | CN | $SO_2-\phi$ | " |
| 20 | H | $n-C_4H_9$ | CN | $SO_2-\phi$ | " |
| 21 | 3-Br | $C_2H_5$ | CN | CN | " |
| 22 | 3-Br | $n-C_4H_9$ | CN | $COOC_2H_5$ | " |
| 23 | 3-Cl | $CH_3$ | CN | CN | " |
| 24 | 3-Cl | $C_2H_5$ | CN | CN | " |
| 25 | 3-Cl | $C_2H_5$ | $CH_3CO$ | $COOC_2H_5$ | " |
| 26 | $3-CH_3CONH$ | $C_2H_5$ | CN | CN | " |
| 27 | $3-CH_3CONH$ | $C_2H_5$ | CN | $COOC_2H_5$ | " |
| 28 | $3-CH_3CONH$ | $C_2H_5$ | $COOC_2H_5$ | $COOC_2H_5$ | " |
| 29 | $3-NO_2$ | $C_2H_5$ | CN | CN | " |
| 30 | $3-CH_3$ | $C_2H_5$ | CN | CN | " |
| 31 | H | $CH_2-\phi-NO_2$ | CN | CN | " |
| 32 | H | $CH_2-\phi-Cl$ | CN | CN | " |
| 33 | H | $-CH_2CH_2CN$ | CN | CN | " |

EXAMPLE 7

The compound of Example 6 was ball-milled with its own weight of a commercially available ligninsulfonic acid dispersing agent ("Lignosol FTA") and enough water to make a mixture 15% by weight dye. The mixture was milled to a thin paste.

The paste when applied to polyester fabric by the recognized methods (carrier, pressure or thermofix) gave bright greenish-yellow dyeings which showed excellent sublimation and light fastness.

EXAMPLES 8–10

By substituting an equivalent amount of the compound of Example 6 for the compound of Example 1, otherwise following the procedures of Examples 3–5, respectively, bright greenish yellow colorations are obtained with methyl methacrylate, polystyrene and polycarbonate.

EXAMPLES 11–46

By substituting equivalent amounts of appropriate reactants in the process of Example 1, the following

TABLE 1A

X and Y in Cyclic Compounds

| Ex. | R | A | $=C<^X_Y$ | HUE |
|---|---|---|---|---|
| 34 | H | $C_2H_5$ |  | Yellow |
| 35 | H | $C_2H_5$ |  | Reddish Yellow |

TABLE 1A-continued

X and Y in Cyclic Compounds

| Ex. | R | A | =C(X)(Y) | HUE |
|---|---|---|---|---|
| 36 | H | n-C₄H₉ | (structure: C=O, N-cyclohexyl, N, CH₃) | " |
| 37 | H | n-C₄H₉ | (structure: C=O, N-(4-Cl-cyclohexyl), N, CH₃) | " |
| 38 | H | C₂H₅ | (structure: C=O, N-cyclohexyl, N, CH₃, CH₃) | " |
| 39 | H | C₂H₅ | (structure: C=O, N-cyclohexyl, N, COOC₂H₅) | " |
| 40 | H | CH₃ | (structure: C=O, NH, C=N, COOC₂H₅) | Reddish Yellow |
| 41 | H | CH₃ | (structure: C=O, N-(3,4-di-OCH₃-cyclohexyl), N, CH₃) | " |
| 42 | H | C₆H₁₁ | (structure: C=O, N-(SO₂NH₂-cyclohexyl), N, CH₃) | " |
| 43 | H | C₂H₅ | (structure: C=O-CH₂, CH₂-C=O) | Yellow |
| 44 | H | C₂H₅ | (phthalimide-type structure) | " |
| 45 | H | C₂H₅ | (structure: C=O-CH₂, CH₂, C-CH₂=O) | " |
| 46 | H | C₂H₅ | (structure: C=O, N-CH₃, C=N, C=O) | Reddish Yellow |

EXAMPLE 47

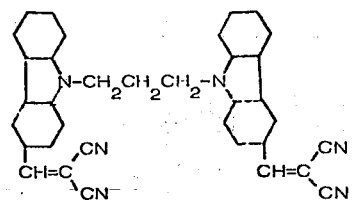

A 1000 ml. 4-neck flask equipped with a thermometer, stirrer, and reflux condenser was charged with 41.0 g. 9,9'-(1,3-propylene)bis-3-carbazolecarboxaldehyde, 150 g. dimethylformamide, 13 g. malonomitrile, 100 g. 2-propanol and 2 ml. piperidine.

The temperature was raised to the boil and stirred at that temperature for three hours. The charge was then cooled to 15°C. yellow crystals separated which were filtered off, washed with 2-propanol, and dried. M.P. 267°–270°C.

EXAMPLE 48–50

Thermoplastic materials such as polystyrene, polycarbonate and methyl methacrylate, are colored in the usual way with the material. Clear yellow hues of good light fastness are obtained on methyl methacrylate, polystyrene and carbonate when the compound of Example 1, otherwise following the procedures of Examples 3–5, respectively.

EXAMPLES 51–62

Following the procedure of Example 47, substituting appropriate reactants, the following compounds are obtained. The compounds applied to methyl methacrylate, polystyrene and polycarbonate by the method of Example 3–5, respectively, yield colored plastics having the hue indicated below:

TABLE 2

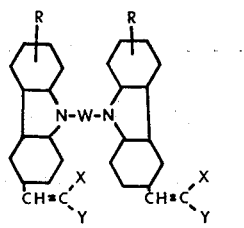

| Ex | R | W | X | Y | HUE |
|---|---|---|---|---|---|
| 51 | H | —CH₂— | CN | CN | Yellow |
| 52 | H | —CH₂CH₂— | CN | CN | " |
| 53 | H | CH₂(CH₂)₄CH₂— | CN | CN | " |
| 54 | H | —CH₂CH₂CH₂CH₂— | CN | CN | " |
| 55 | H | -CH₂-⟨O⟩-CH₂- | CN | CN | " |
| 56 | 3 & 3'-Cl | —CH₂— | CN | CN | " |
| 57 | 3 & 3'-Br | —CH₂CH₂— | CN | CN | " |
| 58 | 3 & 3'-Cl | -CH₂-⟨O⟩-CH₂- | CN | CN | " |
| 59 | H | —CH₂CH₂CH₂— | CN | COOC₂H₅ | " |
| 60 | H | —CH₂CH₂CH₂— | COOC₂H₅ | COOC₂H₅ | " |
| 61 | H | —CH₂CH₂CH₂— | CN | SO₂-⟨O⟩ | " |
| 62 | H | —CH₂CH₂CH₂— | COCH₃ | COOC₂H₅ | " |

What is claimed is:

1. A compound of the formula

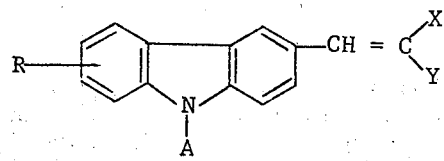

wherein
R is hydrogen, chorine, bromine, nitro or acetamido;
A is lower alkyl, benzyl or cyano(lower alkyl);
X is cyano, lower carbalkoxyl, R₁CO or R₁-SO₂;
Y is lower carbalkoxyl, R₁CO or R₁-SO₂;
X and Y taken together with the carbon to which they are attached are 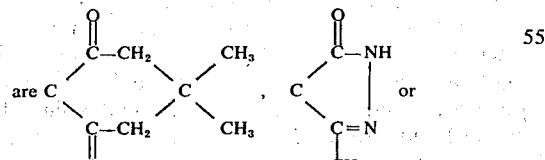 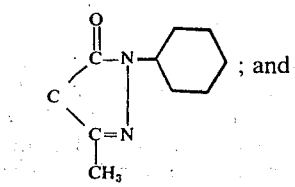; and $R_1$ is a member selected from the group consisting of lower alkyl, chloro(lower alkyl), bromo(lower alkyl), cyano(lower alkyl), phenyl, (lower alkyl)phenyl, chlorophenyl, bromophenyl, nitrophenyl and cyanophenyl.

2. A compound of the formula

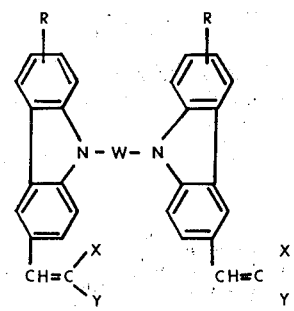

wherein
W is C₁–C₆ alkylene or p-xylylene;
R is hydrogen, chlorine, bromine, nitro or acetamido; each of
X and Y is independently cyano, lower carbalkoxyl R₁CO or R₁-SO₂, R₁ being a member selected from the group consisting of lower alkyl, chloro(lower alkyl), bromo(lower alkyl), cyano(lower alkyl), phenyl, (lower alkyl)phenyl, chlorophenyl, bromophenyl, nitrophenyl, and cyanophenyl; and
X and Y taken together with the carbon atom to which they are attached
are 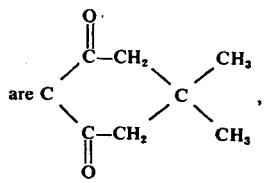, 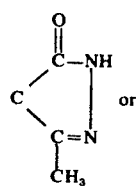 or
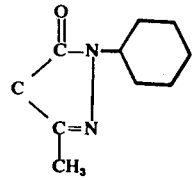
3. The compound of claim 1 wherein R is hydrogen and X and Y are cyano.
4. The compound of claim 1 of the formula
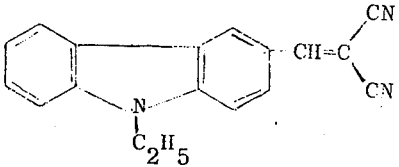
5. The compound of claim 1 of the formula
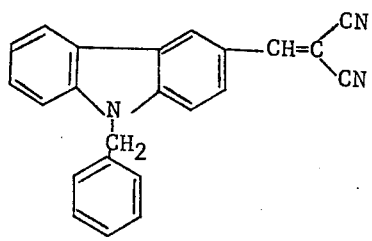
* * * * *